United States Patent
Yiu (10) Patent No.: US 10,045,795 B2
(45) Date of Patent: Aug. 14, 2018

(54) HANDHELD COSMETIC DEVICE WITH PIVOTING HEAD

(71) Applicant: SOFT LINES INTERNATIONAL, LTD., Kowloon (HK)

(72) Inventor: Wai Wah Yiu, Kowloon (HK)

(73) Assignee: SOFT LINES INTERNATIONAL, LTD., Kowloon (HK)

( * ) Notice: Subject to any disclaimer, the term of this patent is extended or adjusted under 35 U.S.C. 154(b) by 0 days.

(21) Appl. No.: 15/093,610

(22) Filed: Apr. 7, 2016

(65) Prior Publication Data

US 2017/0290606 A1 Oct. 12, 2017

(51) Int. Cl.
*A61B 17/54* (2006.01)
*A45D 29/05* (2006.01)

(52) U.S. Cl.
CPC .............. *A61B 17/54* (2013.01); *A45D 29/05* (2013.01)

(58) Field of Classification Search
CPC ........ A45D 29/04; A45D 29/05; A45D 29/14; A61B 17/54; B26B 19/048; B26B 19/063
USPC ....... 132/73.6; D28/58–59; 606/131; 50/73.6
See application file for complete search history.

(56) References Cited

U.S. PATENT DOCUMENTS

| | | |
|---|---|---|
| 1,482,837 A | 2/1924 | Buck |
| 2,395,296 A | 2/1946 | Schwab |
| 2,867,214 A | 1/1959 | Wilson |
| 2,936,768 A | 5/1960 | Chamberlain |
| 3,581,393 A | 6/1971 | Yager |
| 3,635,811 A | 1/1972 | Lane |
| D287,298 S | 12/1986 | Kibe et al. |
| 4,935,184 A | 6/1990 | Sorensen |
| 5,033,485 A | 7/1991 | Hauerwas et al. |
| 5,281,233 A | 1/1994 | Dolev |
| 5,377,699 A | 1/1995 | Varnum |
| 5,383,273 A | 1/1995 | Muller et al. |
| D409,335 S | 5/1999 | Slater |
| 5,918,607 A | 7/1999 | Zucker |
| 5,976,157 A | 11/1999 | Yiu |
| 6,055,731 A | 5/2000 | Zucker |

(Continued)

FOREIGN PATENT DOCUMENTS

| | | |
|---|---|---|
| CN | 101116576 | 2/2008 |
| CN | 201051937 | 4/2008 |

(Continued)

OTHER PUBLICATIONS

Emjoi RotoShave, First Electric Razor, www.youtube.com/watch?v=HKxUhMm P_rs&noredirect=1, retrieved on Jan. 6, 2014, 1 page.

(Continued)

*Primary Examiner* — Todd E Manahan
*Assistant Examiner* — Jennifer Gill
(74) *Attorney, Agent, or Firm* — Foley & Lardner LLP (57) ABSTRACT

A cosmetic device includes a housing having a handle portion, a head assembly coupled to the handle portion, and a drum assembly within the head assembly. The drum assembly includes a drum having an outer surface configured to abrade the skin or nails of a user during rotation of the drum. The device further includes a electromechanical drive system located within the housing and configured to rotate the drum. The head assembly is configured to rotate about an axis that is substantially perpendicular to the axis of rotation of the drum.

13 Claims, 6 Drawing Sheets

(56) References Cited

U.S. PATENT DOCUMENTS

| | | | |
|---|---|---|---|
| 6,123,713 A | 9/2000 | Yiu | |
| 6,159,222 A | 12/2000 | Yiu | |
| D443,627 S | 6/2001 | West | |
| 6,301,786 B1* | 10/2001 | Oswald | B26B 19/048 |
| | | | 30/43.92 |
| 6,305,084 B1 | 10/2001 | Zucker | |
| 6,391,034 B1 | 5/2002 | Adamson et al. | |
| 6,436,106 B2 | 8/2002 | Yiu | |
| 6,442,840 B2 | 9/2002 | Zucker | |
| 6,471,712 B2 | 10/2002 | Burres | |
| 6,523,546 B2 | 2/2003 | Jo et al. | |
| 6,551,262 B1 | 4/2003 | Lechtman | |
| D487,661 S | 3/2004 | Signorati | |
| 6,824,461 B1 | 11/2004 | Dolev | |
| 6,824,546 B1 | 11/2004 | Yiu | |
| D499,842 S | 12/2004 | Yiu | |
| D509,626 S | 9/2005 | Yiu | |
| D543,660 S | 5/2007 | Cheung | |
| D556,380 S | 11/2007 | Long | |
| 7,347,211 B1 | 3/2008 | Macklin | |
| D581,596 S | 11/2008 | Sarway | |
| D598,165 S | 8/2009 | Platek | |
| 7,581,545 B1 | 9/2009 | Moldawski et al. | |
| 7,597,696 B2 | 10/2009 | Poran | |
| D611,198 S | 3/2010 | Platek | |
| D626,693 S | 11/2010 | Harbeke | |
| D628,744 S | 12/2010 | Goetschi | |
| D638,166 S | 5/2011 | Martinez De San Vicente | |
| D645,204 S | 9/2011 | Platek | |
| 8,137,363 B2 | 3/2012 | Cho | |
| 8,316,546 B2 | 11/2012 | Oh | |
| D676,200 S | 2/2013 | Yiu | |
| D678,614 S | 3/2013 | Yiu | |
| D681,277 S | 4/2013 | Yiu | |
| D686,370 S | 7/2013 | Yiu | |
| D692,181 S | 10/2013 | Yiu | |
| 8,545,516 B1 | 10/2013 | Winnett et al. | |
| 8,601,696 B2 | 12/2013 | Ben-Ari | |
| D701,648 S | 3/2014 | Yiu | |
| D706,487 S | 6/2014 | Yiu | |
| D706,986 S | 6/2014 | Yiu | |
| D709,650 S | 7/2014 | Yiu | |
| D715,493 S | 10/2014 | Yiu | |
| D715,495 S | 10/2014 | Yiu | |
| D726,372 S | 4/2015 | Yiu | |
| D733,965 S | 7/2015 | Yiu | |
| D737,518 S | 8/2015 | Yiu | |
| D737,519 S | 8/2015 | Yiu | |
| D737,520 S | 8/2015 | Yiu | |
| 2002/0050278 A1 | 5/2002 | Jo et al. | |
| 2002/0107527 A1 | 8/2002 | Burres | |
| 2004/0181241 A1 | 9/2004 | Jo et al. | |
| 2004/0185067 A1 | 9/2004 | Daikuzono | |
| 2004/0231160 A1* | 11/2004 | Shiba | B26B 19/046 |
| | | | 30/43.92 |
| 2005/0138821 A1* | 6/2005 | Tsushio | B26B 19/048 |
| | | | 30/527 |
| 2005/0187563 A1 | 8/2005 | Yiu | |
| 2006/0218793 A1 | 10/2006 | Zucker | |
| 2006/0260629 A1 | 11/2006 | Chern | |
| 2007/0125097 A1 | 6/2007 | Habatjou | |
| 2008/0034591 A1* | 2/2008 | Fung | B26B 19/02 |
| | | | 30/43.92 |
| 2008/0187563 A1 | 8/2008 | Levy | |
| 2009/0004953 A1 | 1/2009 | Kinsey | |
| 2009/0141343 A1* | 6/2009 | Leard | F42C 13/02 |
| | | | 359/359 |
| 2009/0182349 A1 | 7/2009 | Poran | |
| 2009/0241343 A1* | 10/2009 | Yamasaki | B26B 19/048 |
| | | | 30/43.92 |
| 2009/0301507 A1 | 12/2009 | Tes et al. | |
| 2010/0175263 A1* | 7/2010 | Shimizu | B26B 19/28 |
| | | | 30/43.92 |
| 2010/0175364 A1* | 7/2010 | Yamamoto | C10J 3/00 |
| | | | 60/39.12 |
| 2010/0269350 A1* | 10/2010 | Iwashita | B26B 19/048 |
| | | | 30/43.92 |
| 2011/0094107 A1* | 4/2011 | Ring | B26B 19/048 |
| | | | 30/43.1 |
| 2012/0060382 A1* | 3/2012 | Beugels | B26B 19/048 |
| | | | 30/527 |
| 2012/0226289 A1* | 9/2012 | Yiu | A61B 17/54 |
| | | | 606/131 |
| 2013/0081645 A1 | 4/2013 | Caviness | |

FOREIGN PATENT DOCUMENTS

| | | |
|---|---|---|
| CN | 101312692 | 11/2008 |
| CN | 101933879 | 3/2013 |
| DE | 37 40 902 | 12/1988 |
| DE | 20104304 U1 | 7/2001 |
| DE | 20 2008 005 686 | 8/2008 |
| EP | 1 707 326 | 10/2006 |
| FR | 2728777 | 7/1996 |
| JP | 48-042304 | 12/1973 |
| JP | 59-137084 | 8/1984 |
| JP | 2006-055489 | 3/2006 |
| KR | 10-2007-0017427 | 2/2007 |
| WO | WO-02/28296 | 4/2002 |
| WO | WO-2004/002339 | 1/2004 |
| WO | WO-2009/065184 | 5/2009 |

OTHER PUBLICATIONS

Images of a ROTOSHAVE razor believed to be on sale more than one year before the filing of the present application, 7 pages.

* cited by examiner

HANDHELD COSMETIC DEVICE WITH PIVOTING HEAD

BACKGROUND

The present disclosure relates generally to the field of cosmetic devices. The present disclosure relates more specifically to a handheld cosmetic device.

Handheld cosmetic devices may be used for a variety of purposes. For example, exfoliation is the removal of dead skin cells from the skin's outer most layers and is part of many cosmetic techniques and procedures. Exfoliation can occur via mechanical removal of the skin, typically by rubbing the skin with an abrasive material. Similar mechanical means may be used to shave unwanted hair and buff nails, although a different type of abrasive material may be required. Existing cosmetic tools may include rigidly fixed components, which cannot adapt to the many contours of the body where the user wishes to utilize the cosmetic device.

Various embodiments disclosed herein are directed to improved cosmetic devices.

SUMMARY

One embodiment relates to a cosmetic device comprising a housing comprising a handle portion, a head assembly coupled to the handle portion, and a drum assembly disposed within the head assembly. The drum assembly further includes a drum having an outer surface configured to abrade skin or nails of a user during rotation of the drum. The device further includes an electromechanical drive system located at least partially within the housing and configured to rotate the drum. The head assembly is configured to rotate about an axis that is substantially perpendicular to the axis of rotation of the drum.

Another embodiment relates to a shaving device comprising a housing comprising a handle portion, a head assembly coupled to the handle portion, and a drum assembly disposed within the head assembly. The drum assembly further includes a drum having an outer surface configured to shave hair of a user during rotation of the drum. The device further includes an electromechanical drive system located at least partially within the housing and configured to rotate the drum. The head assembly is configured to rotate about an axis that is substantially perpendicular to the axis of rotation of the drum.

Another embodiment relates to a cosmetic device comprising a handle portion including a locating bracket having a pair of upstanding wall portions; a head assembly including a lower portion defining an aperture and a drum assembly disposed within the head assembly, the drum assembly including a drum having an outer surface configured to abrade skin or nails of a user during rotation of the drum; a spring member disposed at least partially between the upstanding sidewalls of the locating bracket and including a base portion configured to engage the handle portion and a pair of arms to engage the head assembly; and a retainer pin extending through the upstanding wall portions of the locating bracket and the aperture in the head assembly; wherein the head assembly is configured to pivot about the retainer pin from a normal position in either direction away from the normal position, and wherein the spring biases the head assembly toward the normal position.

BRIEF DESCRIPTION OF THE DRAWINGS

This application will become more fully understood from the following detailed description, taken in conjunction with the accompanying figures, wherein like reference numerals refer to like elements.

DETAILED DESCRIPTION

Before turning to the Figures, which illustrate the exemplary embodiments in detail, it should be understood that the present application is not limited to the details or methodology set forth in the description or illustrated in the Figures. It should also be understood that the terminology used herein is for the purpose of description and illustration only, and should not be regarded as limiting.

Figure 1:
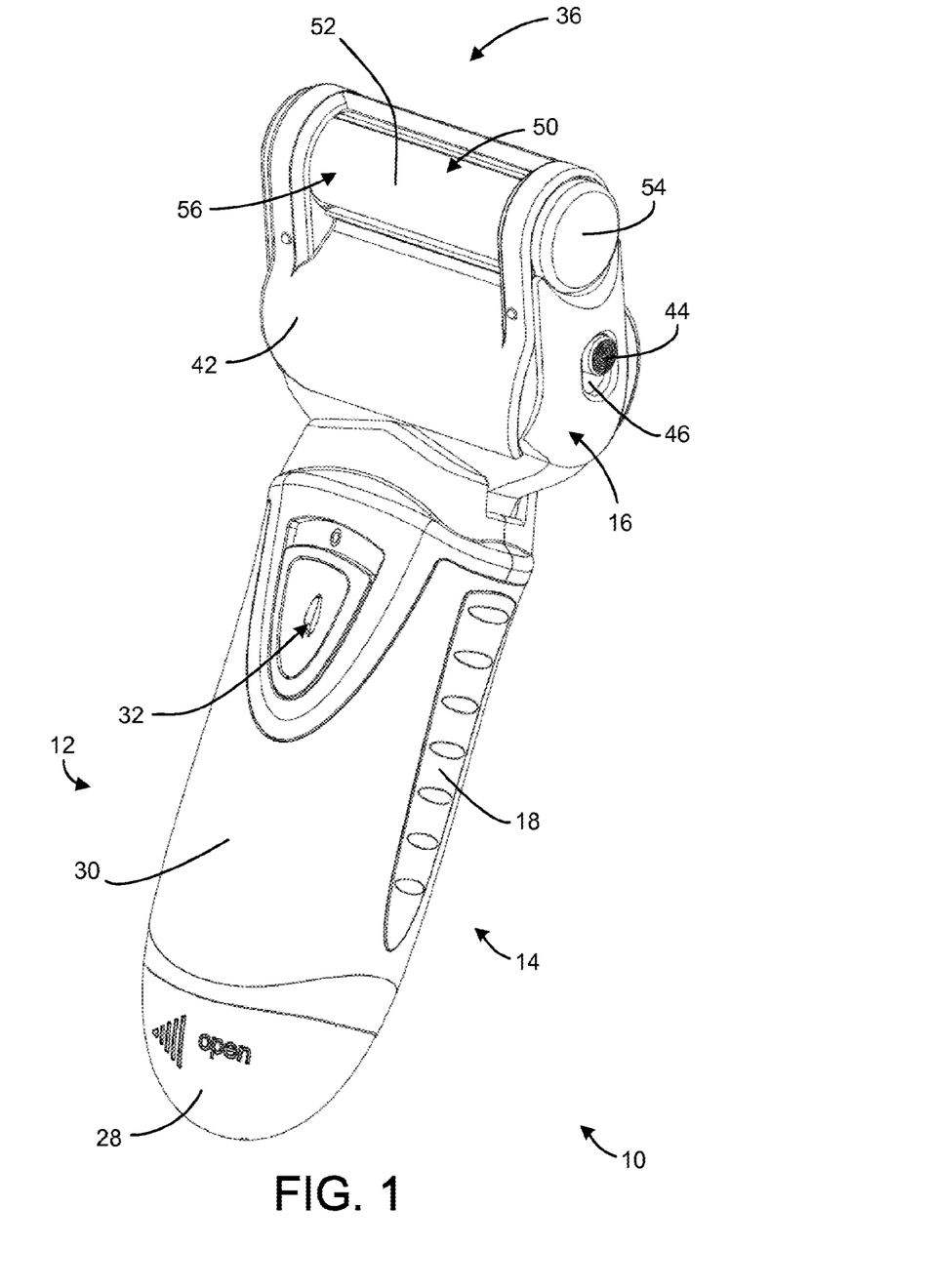
FIG. 1 is a perspective view of a handheld cosmetic device according to an exemplary embodiment.

Referring to FIG. 1, a device for performing personal cosmetic tasks, shown as cosmetic device 10, is depicted according to an exemplary embodiment. Device 10 may be configured for various cosmetic treatments or procedures involving skin removal, hair removal, and nail shaping and buffing. For example, cosmetic device 10 may be a pedicure device configured to remove excess skin or callouses from a person's foot or to shape and buff a person's toenails. In other embodiments, cosmetic device 10 may be configured to remove dead skin or unwanted hair from other parts of the body (e.g., hands, legs, face, etc.). All such applications of device 10 are within the scope of the present disclosure. In the embodiments shown in FIGS. 1-9, cosmetic device 10 is a handheld, electric or automatic cosmetic device in which the exfoliating, shaving, grinding, or buffing motion is supplied by an electro-mechanical drive mechanism (e.g., an electric motor, etc.).

According to an exemplary embodiment, cosmetic device 10 includes a housing 12. Housing 12 generally supports and provides mounting for the various components of cosmetic device 10. In one embodiment, housing 12 defines a handle portion 14 and a head mounting bracket 16. Handle portion 14 is shaped to provide a comfortable gripping structure to allow a user to hold and to manipulate cosmetic device 10 during use. Handle portion 14 includes a pair of opposite lateral sides that may include various gripping features to facilitate grasping of handle portion 14 (e.g., a raised, textured surface, inserts made of a compliant or rubber-like material, etc.). Lateral gripping sections 18 may make holding handle portion 14 easier due to the increased friction between the user's hand and gripping sections 18. At the lower end of handle portion 14, battery door 28 provides access to batteries that provide power to cosmetic device 10.

Still referring to FIG. 1, handle portion 14 of cosmetic device 10 includes a front surface 30 and an activation switch 32 positioned along front surface 30. Activation switch 32 may be toggled between on and off positions, allowing the user to activate and deactivate the exfoliating, shaving, grinding or buffing functions of cosmetic device 10. Activation switch 32 is positioned along front surface 30 between the lateral sides of handle portion 14 such that the user may access activation switch 32 with the user's fingers or thumb while handle portion 14 is grasped within the user's hand. In one embodiment, activation switch 32 may be positioned within a recess formed in front surface 30 of handle portion 14 such that the outer face or surface of activation switch 32 is recessed below front surface 30 of handle portion 14, which may make inadvertent actuation of activation switch 32 less likely.

Figure 2:
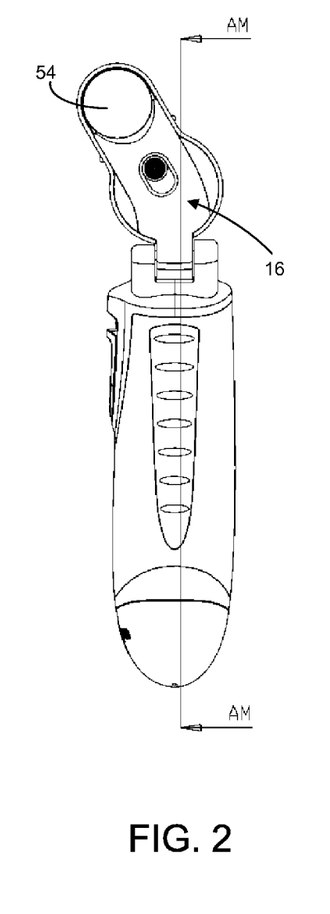
FIG. 2 is a right side view of the cosmetic device of FIG. 1.

Mounting bracket 16 extends from an upper end or portion of handle portion 14. Mounting bracket 16 is coupled to and supports a motor head assembly 36. As best seen in FIG. 2, in one embodiment, mounting bracket 16 is a curved or bent member. Mounting bracket 16 includes a lower section and an upper section positioned at an angle relative to the lower section (e.g., at an angle between about zero degrees and 90 degrees, specifically between about 15 degrees and 45 degrees). In other embodiments, mounting bracket 16 is a generally straight mounting bracket that may be generally aligned with the upper portion of handle portion 14. The shape and size of mounting bracket 16 may be selected to facilitate the positioning of the rotating portion (e.g., the exfoliating head, the shaving head, etc.) of motor head assembly 36 against the user's skin.

Referring further to FIG. 1, in one embodiment, motor head assembly 36 is coupled to mounting bracket 16 such that a user grasping handle portion 14 is able to manipulate and position motor head assembly 36 during use. As described in greater detail below, in some embodiments, motor head assembly 36 may be flexibly coupled to handle portion 14 such that motor head assembly 36 may rotate with respect to handle portion 14. Motor head assembly 36 includes a housing 42 that generally provides support for the components of motor head assembly 36. Motor head assembly 36 also includes a post 44 extending from one of the lateral sides of motor head assembly 36. Mounting bracket 16 includes an aperture 46 that receives post 44. Aperture 46 may facilitate location of motor head assembly 36 relative to mounting bracket 16 during assembly and also provides engagement that substantially fixes motor head assembly 36 in place relative to mounting bracket 16.

Motor head assembly 36 further includes drum assembly 50. Drum assembly 50 includes a head used for exfoliating, shaving, grinding, buffing, etc., shown as drum 52, and an end hub 54 coupled to one of the lateral ends of drum 52. Drum 52 is the rotating element of drum assembly 50 and is rotatably coupled to end hub 54. In the embodiment shown, drum 52 is a cylindrical structure that is rotatably mounted such that drum 52 is allowed to rotate relative to housing 42 of motor head assembly 36. When motor head assembly 36 is coupled to mounting bracket 16 as shown in FIG. 1, at least a portion of drum 52 is positioned above the upper end of mounting bracket 16 and located at the upper end of cosmetic device 10. Drum 52 includes an outer surface 56 configured to remove or abrade (e.g., grind, pulverize, etc.) skin, hair, and nails, providing the functionality of device 10. In one embodiment, drum 50 and/or drum 52 are configured to be inserted and/or removed in a lateral direction, permitting the drum or its outer surface to be cleaned, maintained, replaced, etc.

In one embodiment, outer surface 56 of drum 52 may be or include a coating and may be formed by embedding or affixing a gritty material, such as pumice, directly to the outer surface of drum 52. In another embodiment, a sheet of abrasive material (e.g., a sandpaper-like material) may be adhered to drum 52 to form outer surface 56. In still further embodiments, outer surface 56 may be comprised of cutting devices (e.g., razor blades) for the purpose of shaving hair. The cutting devices may include guard wires or other safety features to prevent the user from accidentally cutting skin. In another embodiment, cosmetic device 10 may include a plurality of drum assemblies 50, each having a different outer surface 56. For example, the plurality of drum assemblies may provide different levels of coarseness or abrasiveness, or may facilitate use of device 10 to perform different cosmetic functions (e.g., one drum assembly for shaving, one drum assembly for buffing, etc.). In this embodiment, the user may select and install a drum assembly 50 depending on the user's desire or need for a particular function. In one embodiment, a drum assembly such as that shown and described in U.S. Pat. No. 8,551,117, entitled "Handled Exfoliating Device" and incorporated herein by reference in its entirety, may be used.

Referring now to FIG. 2, a side view of cosmetic device 10 is shown, according to an exemplary embodiment. FIG. 2 permits a view of drum assembly end hub 54, as well as mounting bracket 16. As shown in FIG. 2, mounting bracket 16 includes a lower section and an upper section positioned at an angle relative to the lower section (e.g., at an angle between about zero degrees and 90 degrees, specifically between about 15 degrees and 45 degrees).

Figure 3:
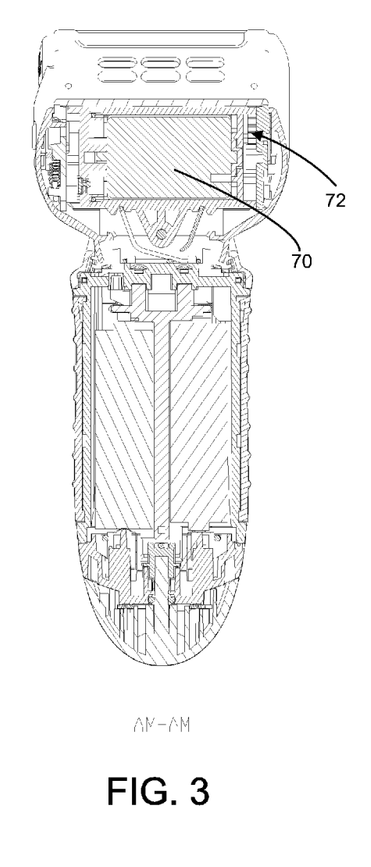
FIG. 3 is a rear sectional view of the cosmetic device of FIG. 1 taken along line AM-AM shown in FIG. 2.

Referring now to FIG. 3, a cross-sectional view of device 10 taken along line AM-AM of FIG. 2 is shown. According to an exemplary embodiment, an electro-mechanical drive system is utilized to rotate drum assembly 50. For example, in one embodiment, motor head assembly 36 may include an electric motor 70, a series of gears 72, and a drive shaft. Drum assembly 50 includes a cavity defined within the body of drum 52, and the drive shaft is received within the cavity of drum 52. Gears 72 are coupled to an output shaft of electric motor 70 and to the drive shaft. Gears 72 transmit rotational motion from electric motor 70 to the drive shaft. Drum 52 is rigidly coupled to the drive shaft such that rotation of the drive shaft causes a corresponding rotation of drum 52. The drive shaft and drum may be coupled in the manner shown in U.S. Pat. No. 8,551,117 according to one embodiment.

In use, upon a user activating device 10 (e.g., via activation of switch 32), motor 70 causes drum 52 to rotate, and the user places the outer surface 56 of drum 52 in contact with the skin, hair, or nail that the user wishes to remove. As drum 52 rotates, outer surface 56 of drum 52 cuts or abrades the skin, hair, and nails, resulting in removal of dead skin cells, removal of unwanted hair, and the shaping and buffing of nails.

In one embodiment, the drive shaft is permanently coupled to gears 72, and drum assembly 50. Drum assembly 50, and specifically drum 52, is removably coupled (i.e., not permanently coupled to) to the drive shaft. This configuration allows drum assembly 50 to be removed and replaced while the drive shaft remains in place coupled to gears 54. This allows the user to switch between drums having different properties by exchanging the drum assembly 50 currently coupled to motor head assembly 36. This configuration also allows for the replacement of an old drum 52 with a drum assembly 50 having a new drum 52 without requiring the drive shaft to be decoupled from motor head assembly 36. Because the drive shaft remains coupled to gears 72 after drum assembly 50 has been removed, the drive shaft may act as a locating feature helping the user to align the new drum assembly 50 during assembly to ensure it is properly installed relative to motor head assembly 36. Further, drum assembly 50 may be easier to manufacture and less expensive than a head assembly having a permanently attached drive shaft.

Figure 4:
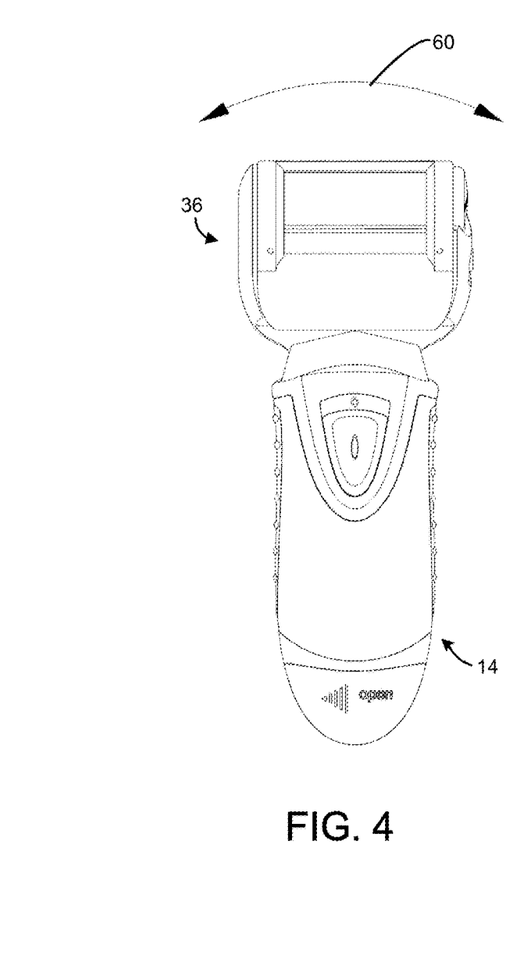
FIGS. 4-6 are front views of the cosmetic device of FIG. 1 depicting the rotational capabilities of the head assembly relative to the handle assembly.
Figure 5:
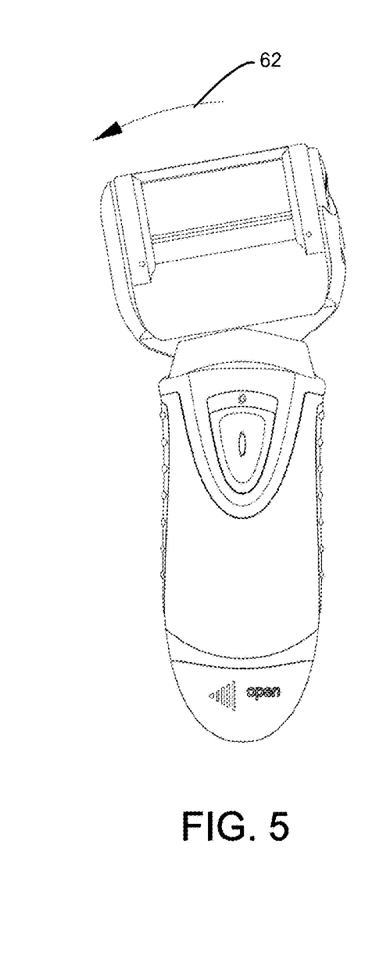
Figure 6:
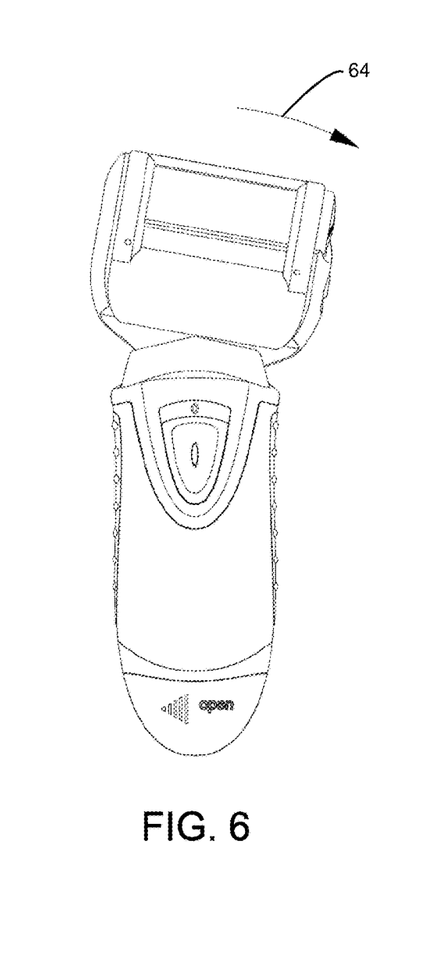

Referring now to FIGS. 4-6, front views of cosmetic device 10 depicting the ability of motor head assembly 36 to rotate relative to handle portion 14 are shown, according to an exemplary embodiment. In some embodiments, motor head assembly 36 is not rigidly fixed to handle portion 14, but instead is flexibly coupled to allow free rotation. This flexible coupling may act to allow drum 52 to remain in contact with the user's body while in use by rotating in direction of rotation 60. This rotation may facilitate the use of cosmetic device 10 on joints and other contours of the body which would not be as easily reached by a configuration in which motor head assembly 36 was fixedly coupled to handle portion 14.

To illustrate the movement of motor head assembly 36 relative to handle portion 14, FIGS. 5-6 depict front views of cosmetic device 10. FIG. 5 depicts motor head assembly 36 biased to the left due to counterclockwise rotation 62. FIG. 6 depicts motor head assembly 36 biased to the right due to clockwise rotation 64. Although motor head assembly 36 may freely rotate when subjected to a force on the motor head assembly by the user, the neutral position (i.e., the position motor head assembly 36 will return to when not subjected to a rotational force) is a position of no rotation relative to handle portion 14, as depicted in FIG. 4.

Figures 7, 8:
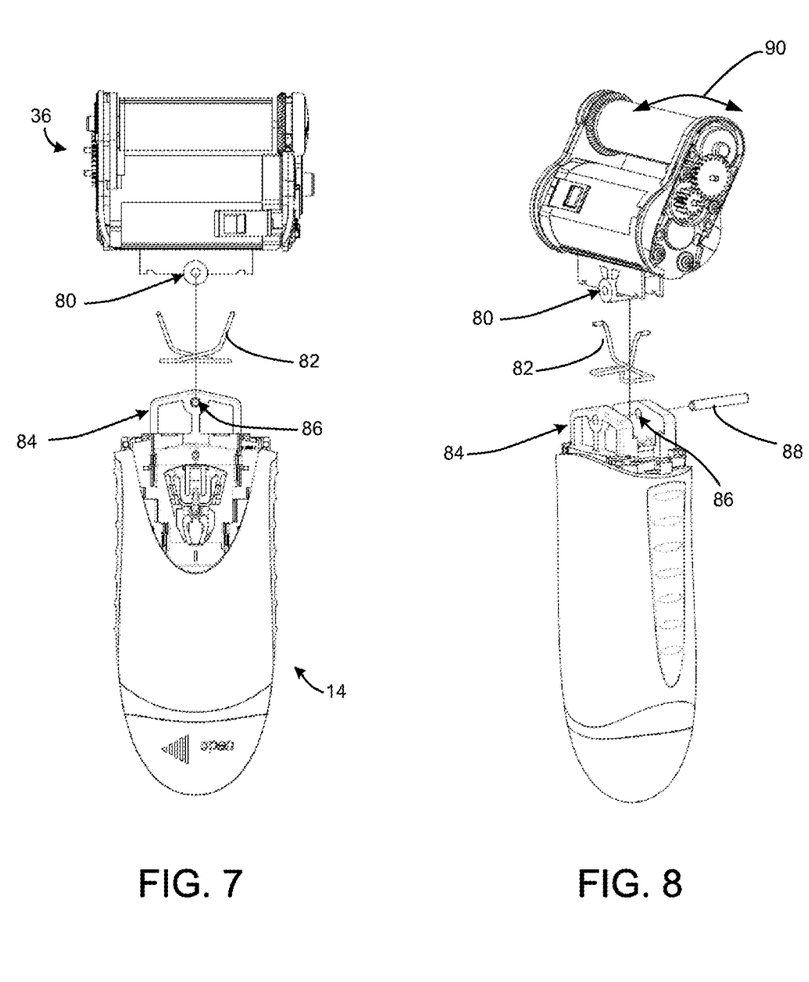
FIG. 7 is a front exploded view of the cosmetic device of FIG. 1 showing partial cut-away views of the head assembly and the handle assembly.
FIG. 8 is a rear perspective exploded view of the handheld cosmetic device of FIG. 1 showing partial cut-away views of the head assembly and the handle assembly.

Referring now to FIGS. 7-8, exploded views of cosmetic device 10 are shown, according to an exemplary embodiment. FIG. 7 depicts a front exploded view, whereas FIG. 8 depicts a rear perspective exploded view. Both FIG. 7 and FIG. 8 depict certain portions of housing 42 of motor head assembly 36 and housing 12 of handle portion 14 in partial cut-away view, in order to aid the visibility of the assembly features used to flexibly couple motor head assembly 36 to handle portion 14. These assembly features include motor head locating hole 80, which is a component of motor head assembly 36, as well as handle locating bracket 84 and handle locating hole 86, which are components of handle portion 14.

Spring 82 forms another assembly feature which may be located between motor head assembly 36 and handle portion 14. Spring 82 may be utilized to keep motor head assembly 36 in a neutral position (e.g., no rotation relative to handle portion 14) when no force is exerted on the motor head. Spring 82 may also provide a slight resistance force in opposition to a force from the user causing motor head assembly 36 to rotate. In order to assemble motor head assembly 36 to handle portion 14, spring 82 may be located between the prongs of handle locating bracket 84. Motor head assembly 36 may then be lowered onto handle portion 14 between the prongs of handle locating bracket 84, until motor head locating hole 80 is substantially concentric with handle locating hole 86.

As shown in FIGS. 7 and 8, spring 82 may in one embodiment be formed from a single piece of resilient material (e.g., a metal, polymer, etc.), and include a base portion that interfaces with handle portion 14 and two upper arms that interface with motor head assembly 36. As shown in FIG. 7, each arm is received in corresponding recesses within motor head assembly 36. As such, the arms provide a biasing force corresponding to the respective directions of flex or rotation that may be used in connection with the use of device 10. According to various alternative embodiments, other shapes and sizes of spring 82 or other biasing mechanisms may be used.

Figure 9A:
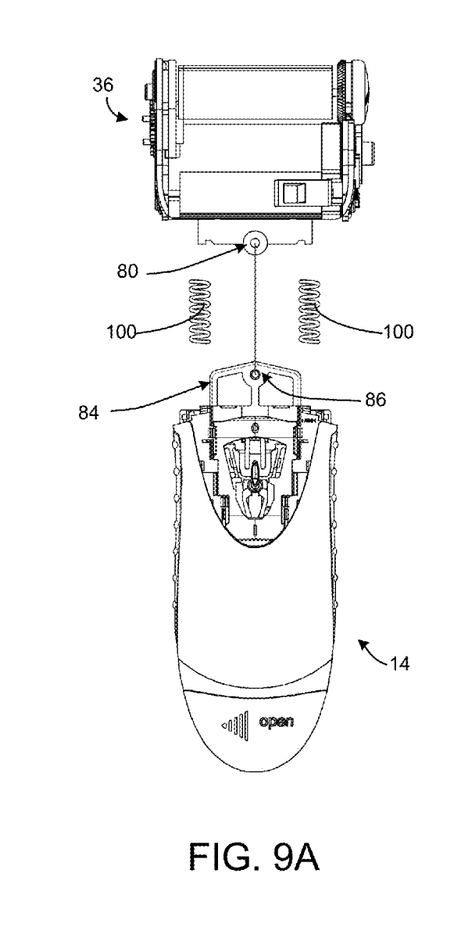
FIG. 9A is a front exploded view of a cosmetic device according to another embodiment.
Figure 9B:
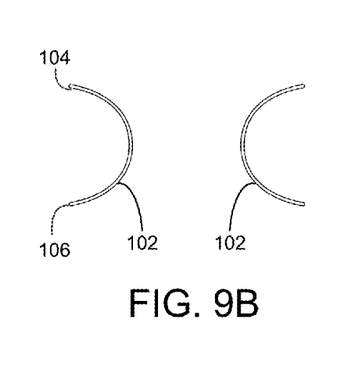
FIGS. 9B and 9C show spring members usable with a cosmetic device according to one embodiment.
Figure 9C:
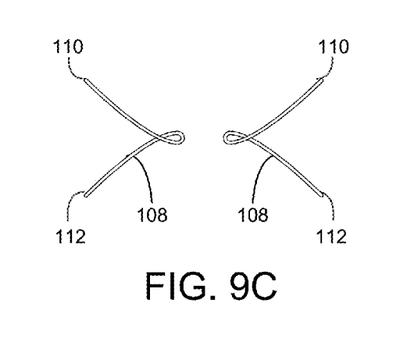

While FIGS. 7-8 generally show spring 82 as being a single spring member having two arms extending up from a base to engage motor head assembly 36, in other embodiments, other types of springs may be used. For example, as shown in FIG. 9A, in one embodiment, device 10 includes two springs 100 disposed on either side of retaining pin 88, such that each spring provides a biasing force to return the device to a normal position. Springs 100 may be coil springs or any other spring that provides a suitable biasing force. For example, as shown in FIGS. 9B and 9C, the springs may include a C-shaped spring 102 configured to engage motor head assembly 36 at a top portion 104 and engage handle portion 14 at a bottom portion 106. Similarly, springs 108 shown in FIG. 9C may be used. Spring 108 may include two generally linear or curved spring portions extending from top portion 110 and bottom portion 112, respectively. Other configurations of single or multiple springs may be used according to various alternative embodiments.

Figure 10A:
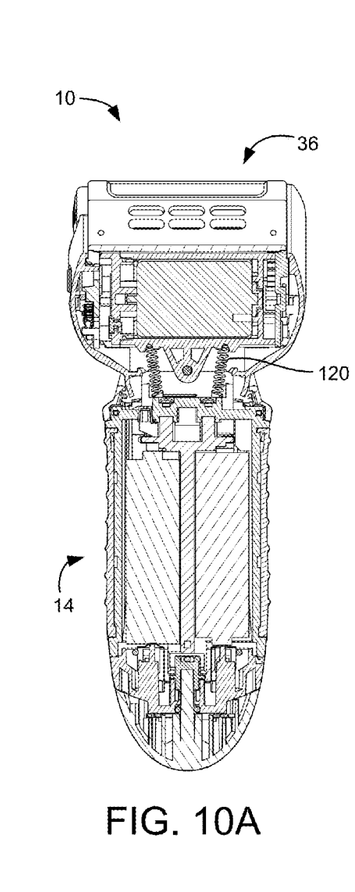
FIGS. 10A-10C show a spring member usable with a cosmetic device according to another embodiment.
Figure 10B:
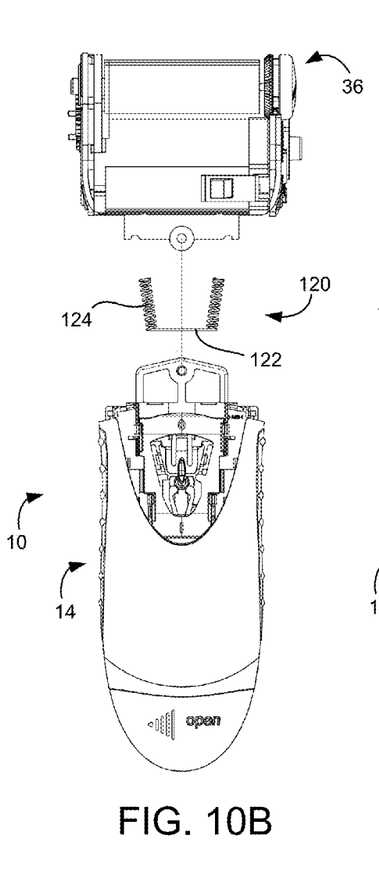
Figure 10C:
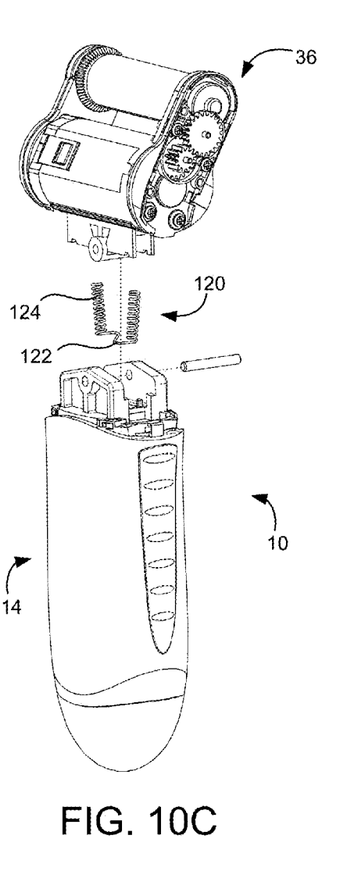

Referring to FIGS. 10A-10C, in some embodiments a spring 120 may be used in connection with device 10 to provide a biasing force between handle portion 14 and motor head assembly 36. As shown in FIG. 10B, spring 120 includes a base portion 122 and two upstanding spring portions 124 extending upward from the base portion 122. The base portion 122 may be straight, serpentine-shaped (e.g., S-shaped), Z-shaped, or have any other suitable shape. The upstanding spring portions 124 may be coil springs or any other suitable spring type. Spring 120 tends to bias handle portion 14 and motor head assembly 36 to a normal position (e.g., aligned, or non-pivoted).

FIG. 8 additionally depicts retaining pin 88. Retaining pin 88 may be inserted through motor head locating hole 80, handle locating bracket 84 (e.g., through the opposing upstanding wall portions of the locating bracket), and handle locating hole 86 in order to retain the assembly of motor head assembly 36 and handle portion 14 and complete the assembly process. Retaining pin 88 may be retained within the assembly by a frictional force between the pin and the locating holes, and the complete symmetry of the pin in the circumferential direction permits motor head assembly 36 to freely rotate relative to handle portion 14 along an axis parallel to the longitudinal axis of the pin. (By contrast, drum 52 may rotate in a perpendicular direction to the rotation of motor head assembly 36, as indicated by rotation 90 in FIG. 8.) However, in further embodiments, motor head assembly 36 may be fastened to handle portion 14 using a variety of mechanical means, including screws, bolts, spring pins, detent pins, etc.

In some embodiments, device 10 provides for a removeable or replaceable head assembly, such as head assembly 36, such that a user may remove or replace the head assembly for a new or different head assembly. In some embodiments, multiple head assemblies 36 may be provided with a single handle portion 14. For example, separate head assemblies may be provided for hair care, skin care, and nail care. Alternatively, rather than providing multiple head assemblies, different drum assemblies may be provided. For example a single device may be provided with multiple drum assemblies, and the drum assemblies may differ in an abrasiveness, hardness, or surface type (e.g., a shaving surface versus an abrading surface). All such combinations of features are to be deemed within the teachings of the present disclosure.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A cosmetic device comprising:
a housing comprising a handle portion, the handle portion including a handle locating hole;
a head assembly coupled to the handle portion, the head assembly including a motor head locating hole;
a spring positioned between the head assembly and the handle portion and configured to position the head assembly relative to the handle portion, wherein the spring is a single unitary piece of resilient material and includes a generally flat spring base and a pair of spring arms extending upward from the spring base;
an elongated retaining pin extending through the handle locating hole and the motor head locating hole and defining a pivot axis extending through the handle locating hole and the motor head locating hole;
a drum assembly disposed within the head assembly and comprising a drum having an outer surface configured to abrade skin or nails of a user during rotation of the drum; and
a motor at least partially disposed within the housing and configured to rotate the drum;
wherein the head assembly rotates about the pivot axis, wherein the pivot axis is substantially perpendicular to an axis of rotation of the drum, such that the head assembly is pivotally movable relative to the handle portion.

2. The device of claim 1, wherein the outer surface of the drum comprises an abrasive material.

3. The device of claim 1, wherein the drum assembly is insertable into and removable from the housing via a lateral side of the handle portion.

4. The device of claim 1, wherein the motor is coupled to the drum assembly via a plurality of gears.

5. The device of claim 1, wherein the motor is configured to rotate the drum via a drive shaft received in a recess formed in the drum assembly.

6. The device of claim 5, wherein the drive shaft may be configured to act as a locating feature for the drum assembly.

7. The device of claim 1, wherein the spring member further provides resistance to rotation of the head assembly about an axis substantially perpendicular to the axis of rotation of the drum.

8. A handheld cordless cosmetic device comprising:
a housing including a handle portion, wherein the handle portion includes a handle locating hole;
a head assembly coupled to the handle portion, wherein the head assembly includes a motor head locating hole;
a spring member positioned between the head assembly and the handle portion and configured to position the head assembly relative to the handle portion, wherein the spring member is a single unitary piece of resilient material and includes a generally flat spring base and a pair of spring arms extending upward from the spring base;
a retaining pin extending through the handle locating hole and the motor head locating hole and defining a pivot axis extending through the handle locating hole and the motor head locating hole;
a drum assembly disposed within the head assembly and including a drum having an outer surface configured to remove hair, skin, or nail material of a user during rotation of the drum; and
a motor disposed within the head assembly and configured to rotate the drum;
wherein the head assembly is configured to rotate about the retaining pin, the retaining pin defining a pivot axis substantially perpendicular to the axis of rotation of the drum.

9. The device of claim 8, wherein the spring member further provides resistance to rotation of the head assembly about an axis substantially perpendicular to the axis of rotation of the drum.

10. The device of claim 8, wherein the handle portion includes a locating bracket at a top portion thereof, wherein the spring member is positioned at least partially within an interior formed by the locating bracket, and wherein the retaining pin extends through the locating bracket.

11. A cosmetic device comprising:
a handle portion including a locating bracket having a pair of upstanding wall portions;
a head assembly including a lower portion defining an aperture and a drum assembly disposed within the head assembly, the drum assembly including a drum having an outer surface configured to abrade skin or nails of a user during rotation of the drum;
a motor configured to rotate the drum;
a spring member disposed at least partially between the upstanding wall portions of the locating bracket and including a base portion configured to engage the handle portion and a pair of arms to engage the head assembly, wherein the spring member is a single unitary piece of resilient material and includes a pair of spring arms extending upward from the spring member base portion, and
a retainer pin extending through the upstanding wall portions of the locating bracket and the aperture in the head assembly, wherein the retainer pin defines a pivot axis extending through the upstanding wall portions of the locating bracket and the aperture in the head assembly;
wherein the head assembly is configured to pivot about the retainer pin from a normal position in either direction away from the normal position, and wherein the spring member biases the head assembly toward the normal position.

12. The device of claim 11, further comprising a motor disposed within the head assembly and configured to rotate the drum assembly.

13. The device of claim 11, wherein the head assembly pivots about an axis perpendicular to an axis of rotation of the drum assembly.

* * * * *